United States Patent [19]
Rundfeldt et al.

[11] Patent Number: 6,117,900
[45] Date of Patent: Sep. 12, 2000

[54] USE OF RETIGABINE FOR THE TREATMENT OF NEUROPATHIC PAIN

[75] Inventors: Chris Rundfeldt, Coswig; Reni Bartsch, Ottendorf-Okrilla; Angelika Rostock, Radebeul; Christine Tober, Weinbohla; Rita Dost, Dresden, all of Germany

[73] Assignee: ASTA Medica Aktiengesellschaft, Germany

[21] Appl. No.: 09/406,135

[22] Filed: Sep. 27, 1999

[51] Int. Cl.[7] ................................................. A61K 31/27
[52] U.S. Cl. .............................................................. 514/485
[58] Field of Search ............................................. 514/485

[56] References Cited

FOREIGN PATENT DOCUMENTS 19539861  4/1997  Germany .

Primary Examiner—Phyllis G. Spivack
Attorney, Agent, or Firm—Pillsbury Madison & Sutro LLP

[57] ABSTRACT

The invention relates to the use of 2-amino-4-(4-fluorobenzylamino)-1-ethoxycarbonylaminobenzene of formula I

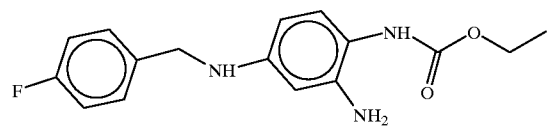

or its pharmaceutically utilizable salts, for the prophylaxis and treatment of neuropathic pain.

8 Claims, No Drawings

USE OF RETIGABINE FOR THE TREATMENT OF NEUROPATHIC PAIN

The invention relates to the use of 2-amino-4-(4-fluorobenzylamino)-1-ethoxycarbonylaminobenzene of the formula I

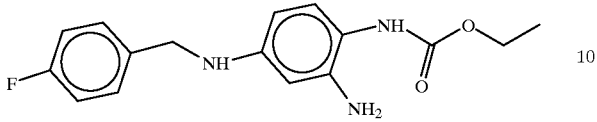

(INN: retigabine)
or its pharmaceutically utilizable salts for the prophylaxis and treatment of neuropathic pain.

Neuropathic pain such as allodynia and hyperalgesia describes a particular type of pain sensation which differs from the customary perception of painful stimuli. Patients who suffer from hyperalgesic pain feel painful stimuli more strongly than healthy people. The term allodynia describes the phenomenon of the perception of stimuli which are not painful per se, such as contact or heat/cold, as pain. In some cases, the perceptions felt are very strong and stressful. This modified pain sensation is covered in German and International usage by various terms which in some cases overlap in their meaning but cannot always be used synonymously. In German usage, the terms Allodynie, Parästhesie, Hyperesthesie, Hyperalgesie and Phantomschmerz (allodynia, paraesthesia, hyperaesthesia hyperalgesia and phantom pain) are customary, in English usage, in addition to allodynia, hyperalgesia and phantom limb pain, the terms reflex sympathetic dystrophy (RSD) (Rogers and Valley, 1994) and sympathetically maintained pain (SMP) are furthermore used (Rogers J N; Valley M A, Reflex sympathetic dystrophy; Clin Podiatr Med Surg. January 1994; 11 (1): 73–83).

Allodynia is understood as meaning the intensified unpleasant to painful perception of stimuli triggered by heat or by contact, which is based on a lowering of the pain threshold for these stimuli only. Hyperalgesia describes the excessive perception of stimuli of all sorts which are painful per se, again on account of a lowering of the pain threshold. Phantom pain is designated as the perception of pain which is non-existent, since, for example, the painful extremity has been amputated. In the scientific literature, this type of pain sensation is often subsumed under the term centrally mediated neuropathic pain. It is characteristic here that the actual pain sensation is not be attributed to a customary pain-inducing stimulus, but is generated by the peripheral or central nervous system, as the level or reaction of the pain-sensing and pain-transmitting system is altered. Unlike other forms of pain, neuropathic pain is usually chronic and customarily cannot be treated or can only be treated with difficulty with conventional analgesics such as opioids.

Disorders in which a modified level of reaction of the pain-sensing and pain-transmitting system is observed can be:

1. Long-lasting allodynia is described as a classical result of the herpes zoster (shingles) infection (Fields et al., 1998; Fields H L; Rowbotham M; Barons R, Posttherapeutic neuralgia: irritable nociceptors and deafferentation. Neurobiol. Dis. October 1998; 5 (4): 209–27).
2. In the case of AIDS patients, in various stages of the disorder pain sensations occur which belong to the hyperalgesia type and are clearly to be differentiated from nociceptive (i.e. induced by painful stimuli) pain (Lefkowitz 1996; Lefkowitz M, Pain management for the AIDS patient. J Fla Med. Assoc. December 1996; 83 (10):701–4).
3. In the parts of the body affected, burn wounds lead to neuropathic hyperalgesias. Although the pain-inducing cause (heat) is no longer present, burn wounds are often extremely painful.
4. After therapy with high doses of cytostatics for cancer treatment, patients often also report pain sensations (Brant 1998; Brant J M, Cancer-related neuropathic pain. Nurse Pract. Forum. September 1998; 9 (3): 154–62). Tanner et al. (Tanner K D; Reichling D B; Levine J D, Nociceptor hyper-responsiveness during vincristine-induced painful peripheral neuropathy in the rat. J. Neurosci. Aug. 15, 1998; 18 (16): 6480–91) were able to show that pain which occurs in connection with vincristine treatment is caused by an increased stimulability of the peripheral pain receptors, that is by hyperalgesia.
5. A tumour disorder itself can also elicit neuropathic pain (e.g. as a result of chronic nerve compression by the tumour) which belongs to the hyperalgesia type (Brant 1998; Brant J M, Cancer-related neuropathic pain. Nurse Pract. Forum, September 1998; 9 (3): 154–62).
6. Trigeminal neuralgia is a widespread form of hyperalgesia which often occurs without visible damage to the nerves (Burchiel, 1993; Burchiel K J, Trigeminal neuropathic pain. Acta Neurochir. Suppl. Wien. 1993; 58; 145–9).
7. In diabetes patients, hyperalgesia often occurs in the course of the disorder as a form of late damage. The patients complain about highly painful limbs with simultaneously reduced contact sensitivity of the skin (Bell 1991; Bell D S: Lower limb problems in diabetic patients. What are the causes? What are the remedies? Postgrad. Med. June 1991; 89 (8): 237–40, 234–4).
8. The diffuse pain occurring in fibromyalgia is subsumed under the term allodynia (Russel, 1998; Russell I J, Advances in fibromyalgia: possible role for central neurochemicals. Am. J. Med. Sci. June 1998; 315 (6): 377–84).
9. A further syndrome in which symptoms of hyperalgesia and allodynia occur is vulvodynia. This disorder is characterized by chronic malaise (burning, stabbing, itching) in the region of the vulva without it being possible to demonstrate that infective agents are the cause (Bohl et al., 1998; Bohl T G, Vulvodynia and its differential diagnoses. Semin. Cutan. Med. Surg. September 1998; 17 (3): 189–95).
10. In patients with chronic back pain, a compression of nerve roots of the spinal cord can often be observed. Apart from in chronic pain, this pressure damage to the nerve roots is also manifested in sensory malaises (paraesthesias). If the restriction is eliminated surgically, in spite of this a large proportion of the patients additionally complain about pain sensations. These persistent sensations are described as neuropathic pain and can be delimited diagnostically from other (inflammatory) forms of pain (Sorensen and Bengtsson, 1997; Sorensen J; Bengtsson M, Intravenous phentolamine test—an aid in the evaluation of patients with persistent pain after low-back surgery? Acta Anaesthesiol. Scand. May 1997; 41 (5): 581–5).
11. In 10 to 20% of patients with spinal cord injuries, in some cases very severe pain sensations result which are generated in the brain for lack of intact spinal cord and are not to be related to a painful stimulus. This pain is described as central neuropathic pain (Eide 1998; Eide P K, Pathophysiological mechanisms of central neuropathic pain after spinal cord injury. Spinal cord. September 1998; 36 (9): 601–12).

12. Pain occurring after amputations has characteristics of neuropathic pain (Hill 1999; Hill A, Phantom limb pain: a review of the literature on attributes and potential mechanisms. J. Pain Symptom Manage. February 1999; 17 (2): 125–42).

13. Internal organs can also be a source of hyperalgesia (Mayer and Gephart, 1994; Mayer E A; Gebart G, Basic and clinical aspects of visceral hyperalgesia [see comments in; Gastroenterology February 1995; 180 (2): 618] Gastroenterology. July 1994; 107 (1): 271–93). Affected patients suffer from inappropriate sensations of physiological reactions in various regions of the gastrointestinal tract, such as, for example, sensation of fullness, stomach pain or the sensation of flatulence, without appropriate pathological causes being present.

As mentioned at the outset, an increased or modified pain reaction is a symptom of various disorders and it appears questionable whether a standard pathogenesis is present. This is also seen in the fact that the nature of the modified pain reaction can be very different. It is common to all these pain reactions, however, that morphines are either inactive or only act when using doses which cause undesired side effects. Triggering factors for the pain reaction can be varied.

In patients with herpes-induced allodynia a draught can be sufficient in order to cause a burning pain. In these patients, it is to be assumed that the causative agents produce damage in neurons, which lowers the pain threshold. In patients with diabetes, it is suspected that the low supply of the nerves with blood and nutrients on account of the microangiopathy leads to chronic nerve damage. This in turn triggers a regeneration process which is manifested in proliferation of nerve fibres.

Reorganization processes in the spinal cord and also peripherally are regarded as a possible cause of hyperalgesias by various authors (see, for example, Basbaum 1999; Basbaum A I, Spinal mechanisms of acute and persistent pain. Reg. Anesth. Pain Med. January–February 1999; 24 (1): 59–67). As a result of chronic compression of nerves, these are damaged without being completely destroyed. While as a result of acute compression local pain signals are triggered, in chronic compression an induction of transcription factors occurs in the cell body (and thus outside the region of the compression in the bone marrow), which lasts for weeks. The neuropeptides such as substance P activate the proliferation of nerve fibres and the activation of unaffected adjacent neurons. Moreover, it was possible to demonstrate that the nerve cell bodies express noradrenaline receptors to an increased extent. As a result, the neurons can become active spontaneously without external initiation and spontaneously trigger pain sensations. After external stimulation, whole discharge volleys are transmitted to the brain instead of individual impulses (Herdegen and Zimmermann, 1995; Herdegen T; Zimmermann M: Immediate early genes (IEGs) encoding inducible transcription factors (ITFs) and neuropeptides in the nervous system: functional networks for long-term plasticity and pain. In: Nyberg F; Sharma H S; Weisenfeld-Hallin Z (Eds.): Neuropeptides in the spinal cord. Progress in Brain Research Vol. 104 Elsevier Publishers, Amsterdam 1995, pp. 299–321).

On account of the participation of noradrenaline receptors, the transmitter substance of the sympathetic system, reference is also made to sympathetically maintained pain, since theses neurons are activated by physiological activation of the sympathetic system. In English usage, the term reflex sympathetic dystrophy (RSD) is therefore widespread (Rogers and Valley, 1994; Rogers J N; Valley M A, Reflex sympathetic dystrophy; Clin. Podiatr. Med. Surg. January 1994; 11 (1): 73–83) or sympathetically maintained pain (SMP). Cytostatics such as vincristine lead directly to an increase in the excitability of peripheral pain receptors and in this way ought to induce hyperalgesia (Tanner et al. 1998; Tanner K D; Reichling D B; Levine J D, Nociceptor hyper-responsiveness during vincristine-induced painful peripheral neuropathy in the rat. J. Neurosci. Aug. 15, 1998; 18 (16); 6480–91).

It has been attempted in animal experiments to elucidate fundamental common mechanisms of hyperalgesia. If, in rats, a peripherally detectable severe hyperalgesia is induced by partial ligature of a nerve branching off from the spinal cord, then superactive groups of neurons are to be found in the spinal cord as ectopically spontaneously active foci (Pan et al., 1999; Pan H L; Eisenach J C; Chen S R, Gabapentine suppresses ectopic nerve discharges and reverses allodynia in neuropathic rats. J Pharmacol Exp Ther. March 1999; 288 (3): 1026–30). By means of gabapentine, a medicament having a marked action in neuropathic pain, the spontaneous activity of these nerve cell foci (ectopic foci) can be suppressed in a dose-dependent manner. In the same dose range, peripheral hyperalgesia is also suppressed. Similar experiments were also carried out in another model (Häbler et al., 1998; Häbler H J; Liu X G; Eschenfelder S; Jänig W. Is sympathetic-sensory coupling in L5 spinal nerve-injured rats direct? Soc. Neurosci. Abstr. 24, 2084). If the spinal nerve L5 was severed, then unexpectedly it was possible to derive spontaneous activity of individual nerve fibres from the nerve stump beginning from day 4 for several weeks. This phenomenon is possibly to be related to phantom pain. Possibly, the spontaneous activity of these nerve fibres after amputation is to be attributed to a disinhibition of the NMDA subtype of the glutamate receptor (Zhuo, 1998; Zhuo M, NMDA receptor-dependent long term hyperalgesia after tail amputation in mice. Eur. J. Pharmacol. May 22, 1998; 349 (2–3): 211–20). Investigations in which it was possible to show that intrathecal administration of NMDA antagonists were able to reduce the pain also point to the involvement of the NMDA receptor. In summary, it can be established that overstimulation conditions of the involved nerves can play a role as a cause of the hyperalgesia or of the modified pain sensation, but the influence of further factors is probable.

In the therapy of these disorders, a completely clear differentiation must be made between the symptomatic treatment of the pain sensation and the nerve cell-protecting treatment of the causes of the disorder (Mörz 1999, Mörz R; Schmerzbehandlung bei diabetischen Neuropathien (Pain treatment in diabetic neuropathies), Fortschritte der Medizin 1999, 13: 29–30). In patients with diabetes-related neuropathic pain, the optimization of the metabolic levels to avoid further progression and the prevention of subsequent damage such as foot lesions is indicated as a basic programme, but this treatment has no effect on the pain symptoms per se.

Furthermore, the cause of the disorder, i.e. the neurodegenerative nerve damage and the underlying microangiopathy can be treated by the use of nerve cell-protecting (neuroprotective) substances such as alpha-lipoic acid or other antioxidants such as vitamin E, vitamins relevant to the nervous system, such as vit. B1, B6 or B12 or by measures improving the circulation, such as physical exercise. This type of treatment does not acutely influence the pain; if, however, an improvement in the nerve function is achieved, it is possible for the pain sensations to subside in the long term.

The actual symptomatic pain therapy, however, must resort to other medicaments. Neither centrally active analgesics such as morphine derivatives nor customary peripherally active analgesics such as paracetamol or acetylsalicylic acid are effective. However, antidepressants such as amitriptyline, imipramine or paroxetine or anticonvulsants such as carbamazepine or gabapentine are employed. Tramadol, as an opioid analgesic, is also effective on account of its further actions on other receptors of the adrenergic system.

In the patent literature, for example, the use of topiramate (U.S. Pat. No. 5,760,007) and moxonidine (EP 901 790) for the treatment of neuropathic pain is demonstrated.

The aim here is to treat the pain symptoms per se and not the causes. All medicaments mentioned, however, only lead to an alleviation of the pain symptoms in some of the patients. In herpes-induced neuropathic pain, it is possible prophylatically by the use of virostatics to protect the nerve cell causally from the harmful action of the virus at an early point in time of the disorder and thereby to reduce the expression of the neuropathic pain; these medicaments, however, are not effective symptomatically after the acute infection subsides. Affected patients can experience alleviation of the symptoms by taking antidepressants, carbamazepine or gabapentine.

In compression-related neuropathic pain, it is possible to eliminate the primary cause of the disorder, for example, in the carpal tunnel syndrome or on compression of spinal cord roots by surgical widening of the narrow sites. On early administration, medicaments having a neuroprotective action can delay or stop the progression of the damage to the nerves. In spite of this, a high proportion of these patients still suffer from pain, which, in turn, does not respond well to classical analgesics, even a long time after the operation. Antidepressants and medicaments such as carbamazepine or gabapentine are used. In the case of amputation pain, the actual cause, the amputation, cannot be treated, so that neuropathic pain has to be treated only symptomatically with the abovementioned groups of medicaments. However, it has been attempted recently in the case of systematic amputations to counteract the development of neuropathic pain by conduction blockade of the nerves to be severed for several days before carrying out the amputation. Although the first indications are positive, the clear demonstration of efficacy in controlled clinical studies has still not been furnished.

In summary, it can be established that for the symptomatic treatment of neuropathic pain conventional analgesics have a low efficacy. Medicaments such as antidepressants, carbamazepine or valproate are used, which per se have no analgesic action on non-neuropathic forms of pain. The treatment of these patients, however, is often not satisfactory.

There is therefore a great need for novel substances for the selective treatment of neuropathic forms of pain.

The aim of this invention is to make available a substance with which the pain symptoms of neuropathic pain can be treated.

Surprisingly, it has now been found that retigabine of the formula I

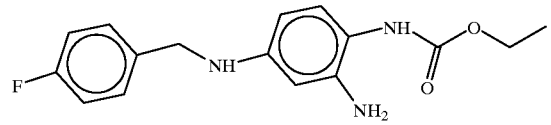

has significant activities against neuropathic pain. Thus entirely new possibilities for the prophylaxis and treatment of neuropathic pain open up.

Retigabine and processes for its preparation have been disclosed (DE 42 00 259).

Retigabine is a derivative of the non-opioid analgesic flupirtine, for which an anticonvulsive action was also demonstrated in addition to its analgesic action. By means of structural optimization with the aim of better separation of desired (anticonvulsant) properties from undesired (analgesic) actions, it was possible using pharmacophore modelling to separate the anticonvulsant from the analgesic action in this substance class. Retigabine has a stronger anticonvulsant action than flupirtine, but an analgesic action in models of acute pain is no longer detectable (Rostock et al., 1996; Rostock A; Tober C; Rundfeldt C; Bartsch R; Engel J; Polymeropoulus E E; Kutscher B; Löscher W; Honack D: White H S; Wolf H H, D-23129: a new anticonvulsant with a broad spectrum activity in animal models of epileptic seizures. Epilepsy Res. April 1996; 23 (3): 211–23).

Retigabine has a broad spectrum of action in experimental models of epileptic attacks (Rostock et al., 1996; Tober et al., 1996; Tober C; Rostock A; Rundfeldt C; Bartsch R, D-23129: a potent anticonvulsant in the amygdala kindling model of complex partial seizures. Eur. J. Pharmacol. May 15, 1996; 303 (3): 163–9) and is in clinical development for the treatment of epilepsy.

In addition, the use of retigabine for the treatment of neurodegenerative disorders is described in EP 857 065.

Unexpectedly, we were able to establish that retigabine has marked dose-dependent action against neuropathic pain. As expected, however, the analgesic action, as is seen in this model in the early phase, was only low and comparable with the reference substance gabapentine.

Pharmacological Investigations

Investigation of the Inhibition of Hyperalgesia in the Rat Formalin Model

In this model, a biphasic nocifensive behaviour reaction is induced by the subcutaneous injection of low-percentage formalin (Field et al. 1997; Field M J; Oles R J; Lewis A S; McCleary S; Hughes J; Singh L; Gabapentine (neurontin) and S-(+)-3-isobutylgaba represent a novel class of selective antihyperalgesic agents. Br. J. Pharmacol. August 1997; 121 (8): 1513–22). The early phase up to at the latest the 10th minute is characterized by intensive licking and biting. The late tonic phase occurs 20–60 min after the injection as the hyperalgesic process stage. The formalin-induced hyperal-

TABLE 1

Effect of retigabine on the hyperalgesia of rats after oral administration

| Treatment | Dose | Sum of the behaviour score over 5 min averaged staring from formalin administration (average value ± standard deviation) | | | | | | | |
|---|---|---|---|---|---|---|---|---|---|
| Time | mg/kg | 5 | 10 | 15 | 20 | 25 | 30 | 35 | 40 |
| 1 Vehicle | — | 35.3 ± 2.76 | 14.9 ± 7.00 | 24.0 ± 7.78 | 30.1 ± 3.91 | 28.9 ± 7.08 | 23.9 ± 7.90 | 23.8 ± 7.61 | 17.5 ± 11.40 |
| 2 Retigabine | 5.0 | 31.9 ± 5.46 | 5.33**± 6.43 | 9.9**± 8.51 | 26.4 ± 6.63 | 21.1 ± 6.15 | 20.6 ± 7.85 | 14.5* ± 7.80 | 10.9 ± 8.98 |
| 3 Retigabine | 10.0 | 25.1**± 6.42 | 2.5** ± 2.78 | 5.6**± 3.46 | 12.9**± 8.49 | 16.5**± 10.49 | 8.8**± 8.91 | 8.4**± 8.47 | 8.3* ± 7.29 |
| 4 Retigabine | 20.0 | 17.6**± 8.52 | 0.9** ± 1.81 | 5.4**± 8.47 | 12.5**± 8.83 | 9.3**± 9.18 | 9.0**± 8.70 | 7.9**± 5.91 | 2.9**± 3.36 |
| 5 Gabapentine | 60.0 | 26.5++± 6.12 | 4.6++ ± 4.53 | 4.5++± 5.76 | 12.4++± 7.11 | 11.5++± 7.27 | 8.4++± 7.76 | 6.8++± 8.76 | 5.6+ ± 9.21 |

Statistical differences in comparison to the vehicle-treated group were carried out for retigabine by means of variance analysis using the following Williams test (*p < 0.05, **p < 0.01)
Statistical differences in comparison with the vehicle-treated group were carried for retigabine by means of Student's t test (+p < 0.05, ++p < 0.01).

gesia includes central mechanisms via sensitization of the neurons in the dorsal horn of the spinal cord, which results as a consequence of the issue damage or increasing activation of the C-afferent fibres.

Field et al. (1997) were able to demonstrate that opioids are inactive in this model against the late phase of hyperalgesic behaviour reactions. On the other hand, the anticonvulsant gabapentine reduced the pain reactions of the rats in a dose-dependent manner.

Investigations With Retigabine
Method

Male Sprague Dawley rats 70–90 g in weight were adapted individually and observed for at least 15 min before the start of the experiment. 0.05 ml of 2.5% formaldehyde in isotonic saline solution given by plantar subcutaneous injection in the hind paw brought about a severe immediate reaction with biting and licking of a few minutes duration with a subsequent hyperalgesic late phase for up to 60 min after the injection of formalin. The biting and licking reactions of the late phase (starting from 10 min) form the measure of the hyperalgesic reactions. These reactions are recorded at 5-minute intervals over the course of 40 min. The test substances were administered orally 60 min before the injection of formalin. The reference substance was gabapentine, 15 animals were employed per group.

Results

Retigabine inhibited the late phase of the pain reactions, to be described as hyperalgesia or neuropathic pain, in a dose-dependent manner after 5, 10 and 20 mg/kg orally. The action of 10 mg/kg of retigabine corresponded approximately to the effect of 60 mg/kg of oral gabapentine (see Table 1).

As with gabapentine, the action on the early phase of the pain, i.e. the analgesic action, was only slight. Thus, the summed pain reactions in the control group in the early phase achieved a behaviour score of up to 35 and in the late phase of up to 30. By means of retigabine, the pain reaction in the early phase was reduced in a dose-dependent manner to 32, 25 and 18, whereas in the late phase almost no pain reaction was any longer detectable with behaviour scores of in some cases below 5.

The pain reaction in the early phase was also lowered only to 27 by gabapentine, whereas in the late phase values of below 6 were also achieved.

Retigabine of the formula I can be converted in a known manner into pharmaceutical formulations such as tablets, capsules, coated tablets, pills, granules, syrups, emulsions, suspensions and solutions, if appropriate using pharmaceutically suitable vehicles and/or excipients.

In the case of oral or parenteral administration, the daily dose of the compound of the formula I should be 50–500 mg. Preferably, individual doses of 30–60 mg are administered in the case of oral administration and 5–20 mg in the case of parenteral administration (the amounts are in each case based on the free base). If necessary, it is possible to depart from the amounts mentioned, namely depending on the body weight and the specific type of administration route.

What is claimed is:

1. A method for preventing or treating pain comprising administering an effective amount of a compound of formula I

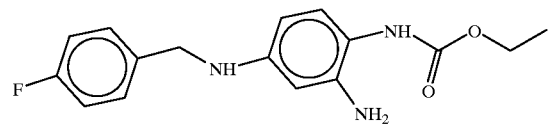

(I)

or a pharmaceutically utilizable salt thereof to an individual in need of such prevention or treatment.

2. The method of claim 1 wherein said pain is selected from the group consisting of neuropathic pain, allodynia, hyperalgesic pain and phantom pain.

3. The method of claim 2 wherein said pain is neuropathic pain.

4. The method of claim 3 wherein said pain is neuropathic pain in migraine.

5. The method of claim 3 wherein said pain is neuropathic pain in diabetic neuropathy.

6. The method of claim 2 wherein said pain is allodynia.

7. The method of claim 2 wherein said pain is hyperalgesic pain.

8. The method of claim 2 wherein said pain is phantom pain.

* * * * *